(12) United States Patent
Lisowsky et al.

(10) Patent No.: US 10,980,239 B2
(45) Date of Patent: Apr. 20, 2021

(54) DECONTAMINATION SOLUTION AND ITS USE FOR DENATURATION, MODIFICATION, DEGRADATION, SOLUBILISATION AND REMOVAL OF PROTEINS, NUCLEIC ACID MOLECULES AND MICROORGANISMS

(71) Applicant: MULTIBIND BIOTEC GMBH, Cologne (DE)

(72) Inventors: Thomas Lisowsky, Monheim (DE); Karlheinz Esser, Moenchengladbach (DE); Richard Lisowsky, Kamen (DE)

(73) Assignee: MULTIBIND BIOTEC GMBH

( * ) Notice: Subject to any disclaimer, the term of this patent is extended or adjusted under 35 U.S.C. 154(b) by 0 days.

(21) Appl. No.: 15/722,153

(22) Filed: Oct. 2, 2017

(65) Prior Publication Data

US 2018/0027818 A1 Feb. 1, 2018

Related U.S. Application Data (60) Continuation of application No. 14/936,713, filed on Nov. 10, 2015, now abandoned, which is a division of application No. 13/867,089, filed on Apr. 21, 2013, now abandoned, which is a division of application No. 11/913,094, filed as application No. PCT/DE2006/000758 on May 2, 2006, now abandoned.

(30) Foreign Application Priority Data

Apr. 30, 2005 (DE) .......................... 102005020327.2

(51) Int. Cl.
| | |
|---|---|
| *A01N 59/16* | (2006.01) |
| *A01N 31/14* | (2006.01) |
| *A01N 43/08* | (2006.01) |
| *A01N 43/78* | (2006.01) |
| *A01N 57/16* | (2006.01) |
| *A61P 43/00* | (2006.01) |

(52) U.S. Cl.
CPC ............ *A01N 59/16* (2013.01); *A01N 31/14* (2013.01); *A01N 43/08* (2013.01); *A01N 43/78* (2013.01); *A01N 57/16* (2013.01)

(58) Field of Classification Search
None
See application file for complete search history.

(56) References Cited

U.S. PATENT DOCUMENTS

| | | | | |
|---|---|---|---|---|
| 4,402,959 A * | 9/1983 | Dybas | ............ | A01N 43/60 514/255.06 |
| 4,510,065 A * | 4/1985 | Sherman | ............ | A01N 43/54 510/112 |
| 4,797,274 A | 1/1989 | Miki et al. | | |
| 5,945,129 A | 8/1999 | Knerr et al. | | |
| 6,296,881 B1 | 10/2001 | Hata et al. | | |
| 6,673,361 B1 | 1/2004 | Ogura et al. | | |
| 6,867,233 B2 | 3/2005 | Roselle et al. | | |
| 7,090,882 B2 * | 8/2006 | Koefod | ............ | A23B 4/0235 426/326 |
| 8,557,265 B2 * | 10/2013 | Krug | ............ | A61K 33/00 424/405 |
| 2003/0162838 A1 * | 8/2003 | Yumioka | ............ | A01N 47/44 514/625 |
| 2004/0101489 A1 | 5/2004 | Nathoo | | |
| 2004/0234621 A1 | 11/2004 | Hwu et al. | | |

FOREIGN PATENT DOCUMENTS

| | | |
|---|---|---|
| DE | 19936428 A1 | 2/2000 |
| DE | 19927936 A1 | 12/2000 |
| EP | 0998937 A2 | 5/2000 |
| FR | 2041 | 4/1962 |
| WO | 99/51585 | 10/1999 |
| WO | 01/24803 | 4/2001 |
| WO | 01/82938 | 11/2001 |
| WO | 03/041499 A2 | 5/2003 |
| WO | 07/080108 A1 | 7/2007 |

OTHER PUBLICATIONS

Van der Werf, Appl Microbiol Biotechnol, 43, pp. 590-594. (Year: 1995).*
EMBL, RNA, obtained online at: https://www.ebi.ac.uk/training/online/course/biomacromolecular-structures-introduction-ebi-reso/ma, downloaded on Jan. 16, 2020. (Year: 2020).*
American Academy of Dermatology Association (AAD), Wrinkles and Other Signs of Sun-Damaged Skin Can Be Treated, obtained online at: https://www.aad.org/public/everyday-care/sun-protection/sun-damaged/wrinkles-sun-damage-can-be-treated, downloaded on Sep. 23, 2020. (Year: 2020).*
Database WPI Week 200350, Derwent Publications Ltd.,London, GB, AN 2003-532627 (May 22, 2003).
Veal, James M. et al: "The influence of reducing agent and 1,10-phenanthroline concentration on DNA cleavage by phenanthroline + copper" in Oxford University Press, Nucleic Acids Research, May 1, 1991, vol. 19, No. 12, pp. 3383-3388.
Padayatty, S.J. et al.: "Vitamin C as an Antioxidant: Evaluation of Its Role in Disease Prevention" in Journal of the American College of Nutrition, 2003, vol. 22, No. 1, pp. 18-35.

(Continued)

*Primary Examiner* — Abigail Vanhorn
(74) *Attorney, Agent, or Firm* — Agris & Von Natzmer, LLP; Joyce von Natzmer (57) ABSTRACT

The invention concerns a three component system comprising surface-active substances, vitamins and metal ions for efficient destruction and removal of contaminating proteins, nucleic acids and microorganisms from surfaces like for example laboratory benches, floors, equipment and instruments. These non-corrosive and non-toxic solutions for removal of proteins, nucleic acids and microorganisms are applied by spraying, rubbing or immersion of contaminated surfaces thereby destroying, solubilizing inactivating and removing proteins and nucleic acids. In that way also microorganisms are killed with high efficiency and at the same time all genetic information is inactivated.

26 Claims, 8 Drawing Sheets

(56) References Cited

OTHER PUBLICATIONS

Blokhina O. et al.: "Antioxidants, Oxidative Damage and Oxygen Deprivation Stress" in Annals of Botany, 2003, No. 91, pp. 179-194.
Perez, et al.: "Ascorbic Acid and Copper: Effective Cytotoxic Agents Against Metastatic Brest Carcinoma (BRCA)Cells" in Proceedings of the Annual Meeting of the American Association for Cancer Research, New York, NY, vol. 42, Mar. 2001, p. 215.
Gonzalez, et al.: "Inhibition of human breast carcinoma cell proliferation by ascorbate and cooper" in Puerto Rico Health Sciences Journal, vol. 21, No. 1, Mar. 2002 pp: 21-23.
Bram, et al.: "Vitamin C Preferential Toxicity for Malignant Melanoma Cells" in Nature, MacMillan Journals, London, GB, vol. 284, No. 5757, 1980 pp. 629-631.
Leung, et al.: "Ascorbic acid with cupric ions as a chemotherapy for human lung tumor xenografts implanted beneath the renal capsule of immunocompetent mice" in In Vivo—International Journal of in vivo research, vol. 6, No. 1, 1992, pp. 33-40.
Satoh, et al.: "Effect of copper and iron ions on cytotoxicity induced by ascorbate, gallate and caffeate" in Anticancer Research, Helenic Anitcancer Institute Athens, GR, vol. 17, No. 3C, 1997 pp. 2181-2184.

\* cited by examiner

DECONTAMINATION SOLUTION AND ITS USE FOR DENATURATION, MODIFICATION, DEGRADATION, SOLUBILISATION AND REMOVAL OF PROTEINS, NUCLEIC ACID MOLECULES AND MICROORGANISMS

CROSS-REFERENCE TO RELATED APPLICATIONS

This is a continuation of US application Ser. No. 14/936,713, which is incorporated herein by reference in its entirety and which is a divisional application of US application Ser. No. 13/867,089, now abandoned, which is a divisional application of US application Ser. No. 11/913,094, now abandoned, and which is the U.S. national stage of International application no. PCT/DE2006/000758, filed May 2, 2006 designating the United States and claiming priority to German application no. 10 2005 020 327.2, filed Apr. 30, 2005.

BACKGROUND OF THE INVENTION

The invention concerns a decontamination solution for the treatment of surfaces that are contaminated by unwanted proteins, nucleic acid molecules or microorganisms. The invention further concerns the use of said decontamination solution and a suitable buffer system.

The dynamic developments in molecular biology stresses the importance of new methods and techniques for detection and amplification of DNA molecules or proteins. [Sambrook, J. et al., eds (1989) *Molecular Cloning: A Laboratory Manual*, 2nd Ed., Cold Spring Harbor Laboratory Press, Cold Spring Harbor, N.Y.]. Latest examples concern medical diagnostics, forensic analysis and biomedical research.

With the invention of the polymerase chain reaction (PCR) it is even possible to detect single molecules. A new problem of the extreme sensitivity of these new detection methods is the contamination of surfaces in laboratories, on equipment or working materials with unwanted nucleic acid molecules, proteins or microorganisms.

In addition microbial contaminations cause severe problems and commercial losses for example in food processing and technology, in production facilities, in hospitals, Hygiene institutes and also in the general household.

PRIOR ART

Therefore already for a longer time many different decontamination solutions exist that use aggressive chemical agents like for example formaldehyde, alcohols, phenols, sodium azide, sodium hypochloride against microorganisms or strong oxidizing agents like for example hypochloride, bleaching substances or mineralic acids that denature proteins and modify nucleic acids thereby rendering them inappropriate for amplification methods like for example the polymerase chain reaction (PCR), nick translation by the klenow polymerase, strand-displacement amplification, ligase chain reaction, transcription-mediated amplification, rolling-circle-amplification and many others more.

The aggressive chemicals and strongly oxidizing agents used for decontamination cause permanent modifications and denaturations of proteins and destabilize and modify the DNA double strand thereby blocking amplification reactions. In general modifications and oxidative damages are introduced at especially reactive chemical groups of the target molecules.

Therefore currently such aggressive chemical solutions are applied for washing and rinsing of equipment, instruments and surfaces.

The major disadvantages of these solutions and methods are the only selective actions against proteins, DNA or microorganisms and the incomplete removal of all nucleic acids molecules, the remaining modified molecules, the only partial degradation and the corrosive effect of the applied chemicals against equipment, instruments, surfaces and also against skin and mucous membranes of the customer.

A limited improvement of the efficiency of these methods was achieved by combining the agents in the solution with surface-active chemicals like detergents. Still the problem of the aggressive chemical substances and the incomplete destruction and removal of nucleic acids, proteins and microorganisms remains.

The commercial interest in such solutions is stressed by the already available and marketed products for decontamination solutions against DNA and protein contaminations as well as anti-microbial agents listed under a large number of different trade marks.

The disadvantages of the currently known decontamination solutions and methods are their only limited action against different biological molecules like proteins or nucleic acids or only anti-microbial actions and the highly corrosive and aggressive chemical potentials in combination with harmful properties that cause severe health problems. Especially for the decontamination of microorganisms there are currently only solutions available that are killing the microorganisms but that do not inactivate or degrade the genetic information, extrachromosomal DNA or proteins.

It is well known that physiological concentrations of micromolar amounts of antioxidants in combination with divalent metal ions result in partial damages and partial breakage of strands in nucleic acids molecules (Podiatry S. J., Katz A., Wang Y., Eck P., Kwon O., Lee J. H., Chen S., Corpse C, Data A, Data S K and Levine M. (2003) Vitamin C as an antioxidant: evaluation of its role in disease prevention. J. Am. Coll. Nut. 1, 18-35; Blocking O., Virolainen E., Fagerstedt K. V. (2003) Antioxidants, Oxidative Damage and Oxygen Depriviation Stress: a Review. Annals Botany 91:179-194; Veal J. M., Merchant K. & Rill R. L. (1991) The influence of reducing agent and 1,10-phenanthroline concentration on DNA cleavage by phenanthroline+copper. Nucl Acids Res Vol. 19, No. 12, 3383-3388). These are only selected and isolated results that can only be applied to specific single cases.

The latest findings in modern molecular biology and gene technology demonstrate that already the genetic information alone single genes or even fragments thereof as well as specific proteins are sufficient to cause diseases or unwanted changes in the genetic information.

Therefore in practice there is a need for new improved protocols, agents, methods and solutions for efficient and at the same time gentle complete decontamination of surfaces and equipment from proteins, nucleic acids and microorganisms.

SUMMARY OF THE INVENTION

An object of the here described invention is therefore to overcome the disadvantages of the prior art and to develop new methods and solutions that do not use aggressive chemicals or highly oxidizing agents and that in addition completely decontaminate the treated substrates.

According to the invention, this object is achieved by a decontamination solution comprising a synergistic mixture of a) at least one vitamin and
b) at least one metal ion and
c) at least one surface-active compound, wherein said mixture has a pH value ranging from pH 2 to 8.5.

By applying natural anti-oxidants in combination with metal ions and surface-active agents, surprisingly, it was found that different vitamins in combination with metal ions and detergents result in an extremely fast and massive strand breakages and modifications in nucleic acid molecules and proteins. This surprising effect leads to efficient killing of microorganisms by inactivation and degradation of their genetic information and proteins. Especially surprising and new is the finding that the three component system of this invention shows inactivation and degradation in the entire pH range of 2 to 8.5 with an essentially comparable efficiency. Since one can work within a comparatively mild range of pH, the solution according to the invention prevents the surface to be treated from damage and is also skin-compatible for the user. By spraying, rubbing or immersion in solutions of the three components, proteins and nucleic acids are denatured, solubilised, inactivated, degraded and removed and thereby also microorganisms are killed with a high efficiency.

In an advantageous embodiment of the invention, it is provided that the mixture has a pH value ranging between pH 3 and 7, preferably between pH 4 and 6. In such pH ranges the solution according to the invention is stable over a long period of time and allows for very efficient degradation of nucleic acids. Additionally, the skin-compatibility of the solution according to the invention is optimal in the range between pH 4 and 6.

Especially preferred is an advantageous embodiment in which the mixture additionally comprises a buffer system including carbonates and derivatives of succinic acid, each preferably in a concentration between 1 mM and 500 mM. Using this buffer system according to the invention with the decontamination solution according to the invention, the pH value of the solution, which is in an acidic range due to the dissolved components, in particular the acidic vitamins, can be increased up to, for example, a neutral or weak basic range without precipitation of the dissolved metal ions.

In a preferred embodiment of the decontamination solution according to the invention, the vitamins or their respective salts or acidic derivates contained in the solution according to the invention are one or several compounds and/or their related salts selected from the group of the water-soluble vitamins with the properties of antioxidants, like preferably vitamin C, riboflavine and niacin. Preferably, they are used in concentrations of 1 mM to 1000 mM in relation to the total volume of the solution, in particular in a concentration of 10 mM to 100 mM.

In a further preferred embodiment of the decontamination solution according to the invention, the metal ions contained according to the invention are di- and/or tri-valent ions of metals found in the 4th group and/or sub-group I, II and VIII of the periodic table of the elements. They are used as salts in combination with their organic and/or inorganic acids and bases. According to the invention, one or several compounds selected from sub-group VIII, especially iron, cobalt, nickel, copper or zinc, are preferred. They are preferably used in concentrations of 1 mM to 100 mM, in relation to the total volume of the solution, in particular in concentrations of 5 mM to 10 mM.

The surface-active substances contained in the solution according to the invention may be, for example, anionic, non-ionic, amphoteric or cationic inert tensides or suitable mixtures thereof or thereunder. Especially, alkylethersulfate, alkyl- and/or arylsulfonate, alkylsulfate, amphotensides, betaines, alkylamidoalkylamines, alkyl substituted amino acids, alkyl substituted imino acids, acylated amino acids, and amphotenside combinations can be used. In principle all inert tensides are suitable. Inert means, that they do not influence the synergistic solution and the experimental outcome. According to the invention, anionic and non-ionic tensides are preferred. They are preferably used in concentrations of 0.1%. to 10% (weight), in relation to the total volume of the solution, in particular in concentrations of 0.2% to 0.5% (weight).

The decontamination solutions according to the invention may comprise additional common inert adjuvants and additives like for example suitable buffer substances for adjusting a specific pH value, like, for example, Tris (Tris(hydroxymethyl)-aminomethan), MES (2(Morpholino)ethansulfonic acid), HEPES (2-[4-(2-Hydroxyethyl)-1-piperazinyl]-ethansulfonic acid, and/or MOPS (3-(N-Morpholino)propansulfonic acid). The buffer systems are used in concentrations of 1 mM to 500 mM in relation to the total volume of the solution.

The efficient action of the new three component system is even more surprising as it is proven that the different isolated substances alone do not exhibit a special degradation effect and also the mixtures of the components outside the range of the invention are not effective or do only show an unsatisfactory effect. Only the combination of vitamins with metal ions and detergents, preferably in an appropriate mixture, results in a synergistic effect and in a rapid and massive degradation of the biomolecules. In particular, by keeping the correct preferred concentrations, an efficient activity of the decontamination solution according to the invention is ensured.

In principle thereby all kind of surfaces can be treated in a very gentle way for removal of proteins, nucleic acids contaminations and microorganisms.

In general decontamination is achieved by spraying or rubbing the inventive solutions onto contaminated surfaces or by immersion. A residence time of 0.5 to 2 minutes at room temperature or slightly higher temperatures is normally sufficient for complete denaturation, modification, degradation, solubilisation and removal of proteins, nucleic acids and microorganisms from surfaces. The applied methods are however variable and can be adjusted to the different tasks.

Another purpose of this invention is the use of the inventive decontamination solutions for denaturation, modification, degradation, solubilisation and removal of proteins, nucleic acid molecules and microorganisms from surfaces.

Figure 5:
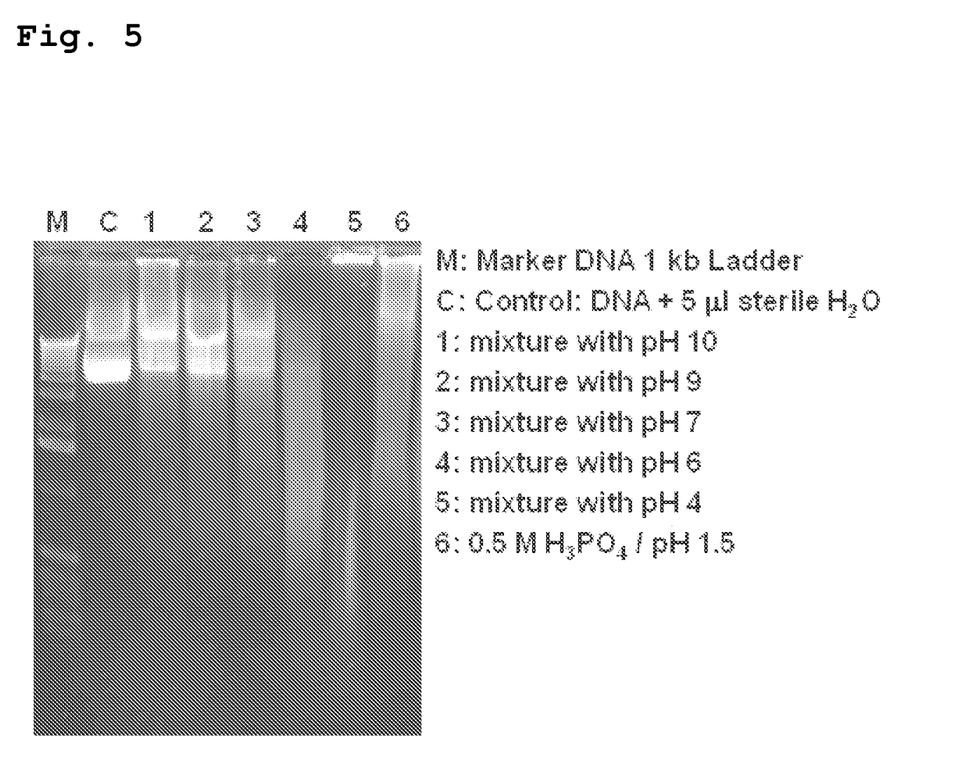

The new and advantageous buffer system with carbonate and derivatives of succinic acid is especially suitable for the decontamination solution of the present invention. The different mixtures with pH values between pH 2 and 8.5 each provide clear solutions of a light yellow to light brown color that are stable over longer periods of time and that also show in particular in the pH range of pH 4.5 to pH 6 a very efficient degradation of DNA molecules as demonstrated in comparison to the strong mineralic 0.5 M phosphoric acid of pH 1.5, as shown in FIG. 5.

In an advantageous embodiment of the buffer system according to the invention, it is provided that the carbonates and derivatives of succinic acid are each provided in concentrations between 1 mM and 500 mM.

The solution comprising the buffer system may be advantageously adjusted to a pH value ranging from pH 2 to 8.5, in particular from 3 to 7, preferably from 4 to 6. Thereby it is ensured that the further components dissolved in the solution are not impaired and additionally a skin-compatible solution can be prepared.

Therefore, the invention also concerns a method for adjusting the pH value of a solution which comprises a mixture of a) at least one vitamin, and
b) at least one metal ion, and
c) at least one surface-active substance, wherein the mixture can be adjusted by the buffer system according to the invention to a pH value ranging from 2 to 8.5, in particular from 3 to 7, preferably from 4 to 6.

BRIEF DESCRIPTION OF THE FIGURES

The invention is illustrated by nonrestrictive figures, examples and tables shown in the following part.

In that case

Table 1 shows a test for the anti-microbial action of the new three component system.

Table 2 shows the preferred basic composition and the preferred mixtures for the three component system containing detergents, vitamins and metal ions.

DESCRIPTION OF ADVANTAGEOUS AND PREFERRED EMBODIMENTS OF THE INVENTION

FIGS. 1 to 5 show the efficient degradation of DNA molecules by the new three component system in comparison with known other solutions. Identical aliquots of DNA plasmids (YEp351) were treated for 2 minutes with the listed solutions. Afterwards the DNA samples were denatured and the single-stranded DNA molecules were separated by gel electrophoresis on an agarose gel (1%). After staining with ethidium bromide the listed pictures were produced. The control shows intact plasmid DNA after treatment with sterile water. Introduction of nicks into the DNA strand results in a reduction of the size and molecular weight of the respective DNA molecules. This effect can be identified in the gel by comparison with the control and the molecular weight marker. In each sample 5 µg DNA were present in 5 µl sterile Tris buffer (1 mM; pH 8.0) and were treated for 2 minutes at room temperature with 5 µl of the listed solutions. Subsequently the samples were mixed with 5 µl 100 mM Tris (pH 12) and bromphenol blue marker and were denatured for 5 minutes at 95° C. The denatured samples were immediately cooled to 4° C. and identical aliquots of 1 µg DNA were loaded per gel lane. DNA molecules were stained with ethidium bromide after gel electrophoresis in a 1% agarose gel and photographed.

Figure 1:
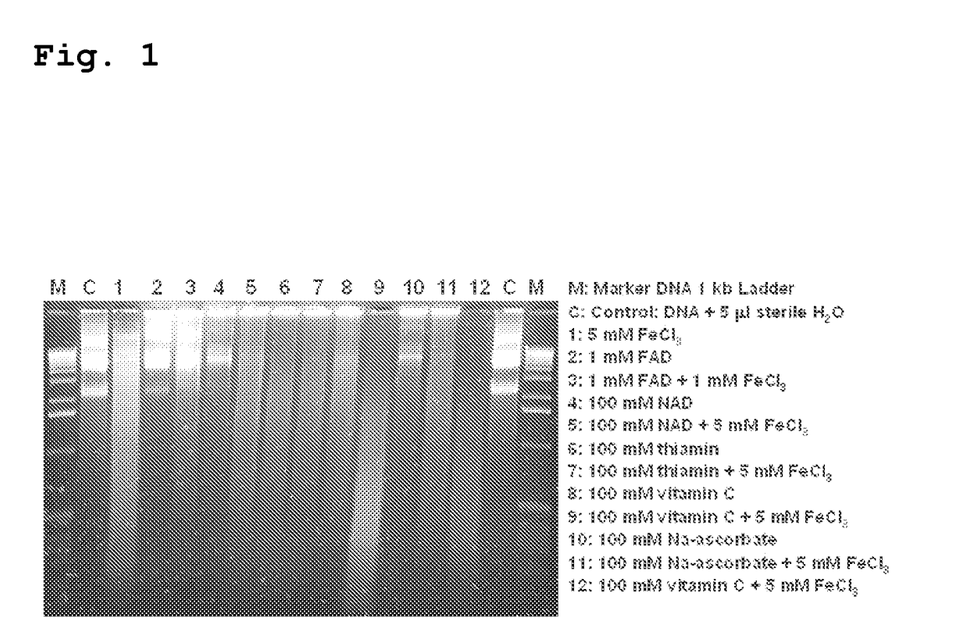
FIGS. 1 to 5 show the efficient degradation of DNA molecules by the three component system in comparison with known other solutions of prior art.

FIG. 1 shows the comparison of nucleic acid degradation by vitamins and metal ions alone and by the three component system containing vitamins, metal ions and detergents. (M: Marker DNA 1 kb ladder; C: Control: DNA+5 µl sterile $H_2O$; 1: 5 mM $FeCl_3$; 2: 1 mM FAD; 3: 1 mM FAD+1 mM $FeCl_3$; 4: 100 mM NAD; 5: 100 mM NAD+5 mM $FeCl_3$; 6: 100 mM thiamin; 7: 100 mM thiamin+5 mM $FeCl_3$; 8: 100 mM vitamin C; 9: 100 mM vitamin C+5 mM $FeCl_3$; 10: 100 mM Na-ascorbate; 11: 100 mM Na-ascorbate+5 mM $FeCl_3$; 12: 100 mM ascorbic acid+5 mM $FeCl_3$). All samples contained 0.2% Triton X-100 and 0.2% Tween 20.

Figure 2:
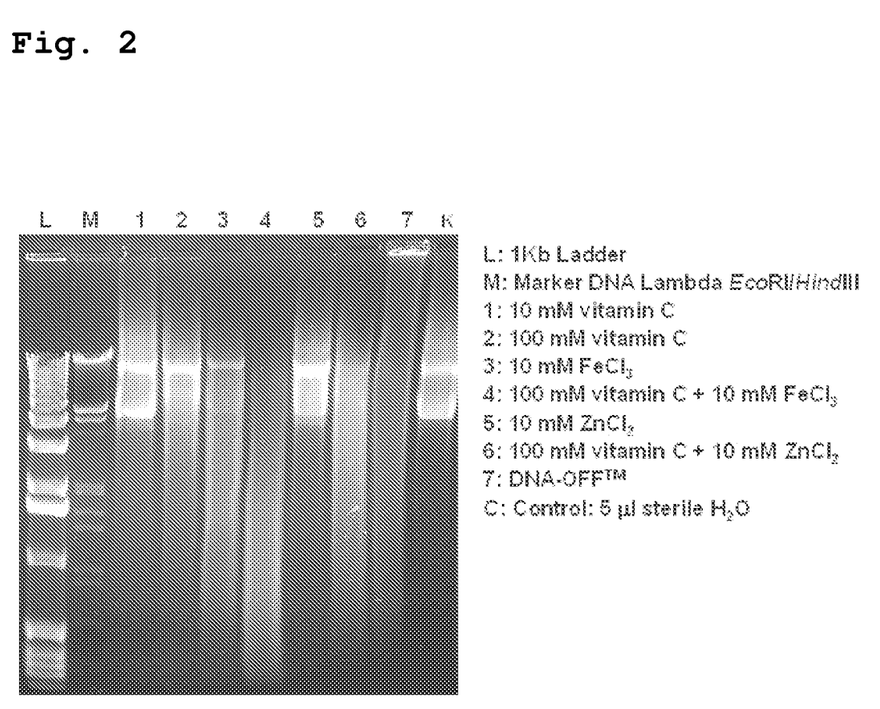

FIG. 2 shows the test for nucleic acid degradation by mixtures containing vitamin C, metal ions and detergents. L: 1 Kb Ladder; M: Marker DNA Lambda EcoRI/HindIII; 1: 10 mM vitamin C; 2: 100 mM vitamin C; 3: 10 mM $FeCl_3$; 4: 100 mM vitamin C+10 mM $FeCl_3$; 5: 10 mM $ZnCl_2$; 6: 100 mM vitamin C+10 mM $ZnCl_2$; 7: DNA-OFF™; C: Control: 5 µl sterile $H_2O$). All samples contained 0.2% Triton X-100 and 0.2% Tween 20.

Figure 3:
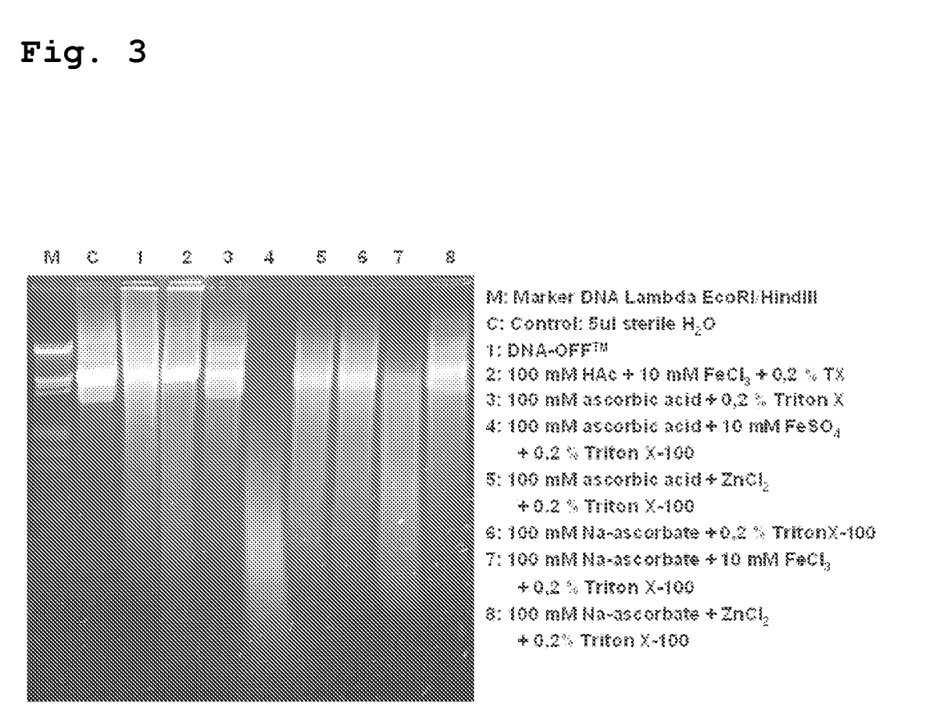

FIG. 3 shows the comparison of nucleic acid degradation by mixtures containing ascorbic acid or Na-ascorbate. (M: Marker DNA Lambda EcoRI/HindIII; C: Control: 5 µl sterile $H_2O$; 1: DNA-OFF™; 2: 100 mM HAc+10 mM $FeCl_3$+0.2% Triton X-100; 3: 100 mM ascorbic acid+0.2% TritonX-100; 4: 100 mM ascorbic acid+10 mM $FeSO_4$+0.2% TritonX-100; 5: 100 mM ascorbic acid+$ZnCl_2$+0.2% TritonX-100; 6: 100 mM Na-ascorbate+0.2% TritonX-100; 7: 100 mM Na-ascorbate+10 mM $FeCl_3$+0.2% Triton X-100; 8: 100 mM Na-ascorbate+$ZnCl_2$+0.2% Triton X-100).

Figure 4:
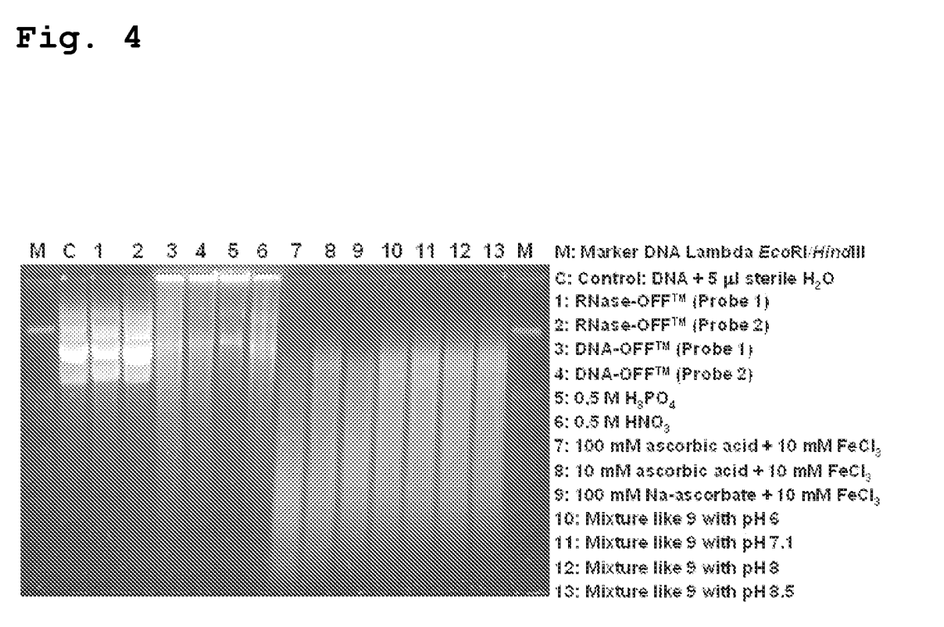

FIG. 4 shows the comparison of nucleic acid degradation by mixtures containing mineralic acids, ascorbic acid or Na-ascorbate (pH 6 to 8.5). (M: Marker DNA Lambda EcoRI/HindIII C: Control: DNA+5 µl sterile $H_2O$; 1: RNase-OFF™ (sample 1); 2: RNase-OFF™ (sample 2); 3: DNA-OFF™ (sample 1); 4: DNA-OFF™ (sample 2); 5: 0.5 M $H_3PO_4$; 6: 0.5 M $HNO_3$; 7: 100 mM ascorbic acid+10 mM $FeCl_3$; 8: 10 mM ascorbic acid+10 mM $FeCl_3$; 9: 100 mM Na-ascorbate+10 mM $FeCl_3$; 10: mixture like in 9 only with pH 6; 11: mixture like in 9 only with pH 7.1; 12: mixture like in 9 only with pH 8; 13: mixture like in 9 only with pH 8.5). The samples number 5 to 13 contained 0.2% Triton X-100 and 0.2% Tween 20.

FIG. 5 shows an example for the new buffer system containing Na-carbonate and malic (hydroxy-succinic) acid in comparison with mineralic acid. The basic mixture contains 50 mM ascorbic acid, 5 mM $FeCl_3$ and 0.2% Triton X-100 and 0.2% Tween 20. (M: Marker DNA 1 kb Ladder), C: Control: DNA+5 µl sterile $H_2O$; 1: mixture with pH 10; 2: mixture with pH 9; 3: mixture with pH 7; 4: mixture with pH 6; 5: mixture with pH 4; 6: 0.5 M $H_3PO_4$ (pH 1.5) with 0.2% Triton X-100 and 0.2% Tween 20.

Figure 6:
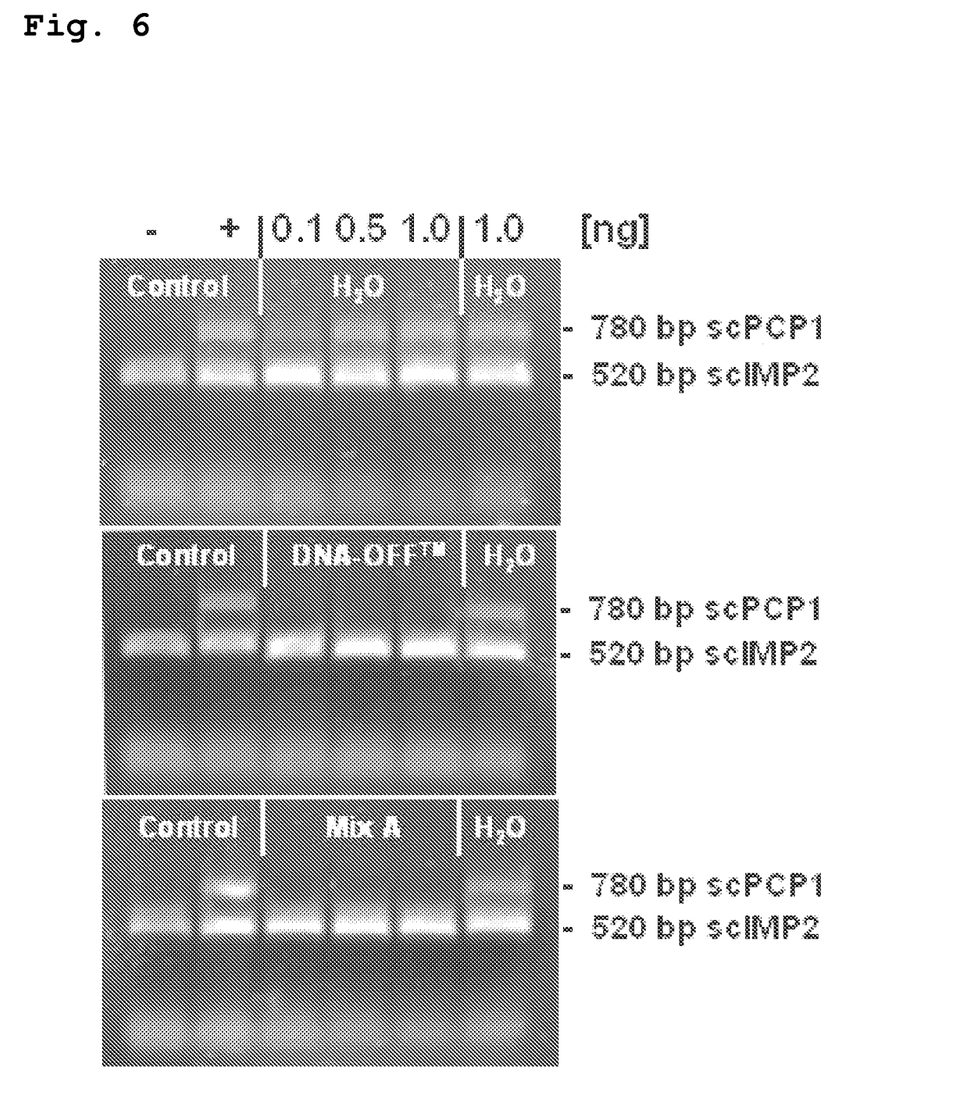
FIG. 6 demonstrates the blockage of PCR amplification of DNA molecules after the treatment with the new three component system.

FIG. 6 shows the blockage of PCR amplification for DNA molecules after treatment with the new three component system (mixture A: 100 mM vitamin C+10 mM $FeCl_3$+0.2% Triton X-100 and 0.2% Tween 20). Different amounts (0.1 to 1 ng) of a DNA sample were dried in PCR tubes. PCR tubes containing the dried DNA were treated for 20 seconds with the listed solutions. Subsequently the tubes were washed two-times with 100 µl of sterile, distilled water. Finally the tubes were filled with a 50 µl PCR reaction mixture and the PCR reaction was performed. The PCR reaction mixture contained pair of primers for the amplification of the control DNA (scIMP2 gene of yeast) and the test DNA (scPCP1 gene of yeast). The control DNA (1 ng) indicates a successful PCR reaction. A band of the test DNA demonstrates that intact DNA molecules for this gene are still present. In case of complete removal or blockage of the test DNA there shall not be any amplified DNA band in the gel.

DNA was stained with ethidium bromide after gel electrophoresis in a 1% agarose gel and the gel was photographed. As a positive control the conventional DNA-OFF™ was used. Sterile water ($H_2O$) served as a negative control.

Figure 7:
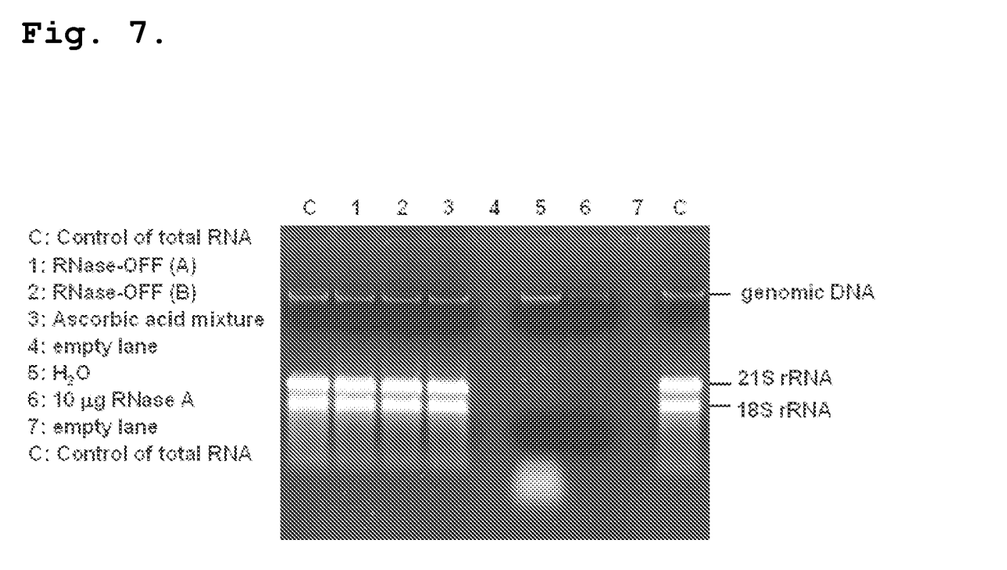
FIG. 7 shows the standard test with RNaseA for enzyme inactivation with the new three component system.

FIG. 7 shows the test of prior art for RNaseA enzyme inactivation in comparison with the new three component system. Identical aliquots of 10 μg RNaseA were dried in Eppendorf tubes. Afterwards each tube was treated with 1 ml of the listed solutions, vortexed for 20 seconds and finally incubated for 5 minutes at room temperature. Subsequently each tube was washed two-times with 1 ml of sterile water. Afterwards 5 μg of total RNA from *E. coli* were added into the tubes and incubated for 30 minutes at 37° C. Subsequently total RNA samples were mixed with formamide/bromphenol blue buffer and denatured at 95° C. for 5 minutes. Afterwards the complete 5 μg total RNA sample was loaded onto an agarose gel (1.2%) and separated by gel electrophoresis. After staining with ethidium bromide the documented picture was taken. The untreated controls represent intact total RNA. In the presence of active RNaseA these RNA molecules are degraded. In case of successful, complete inactivation of RNaseA the total RNA molecules will also remain intact.

(C: Control of total RNA; 1: RNase-OFF (A); 2: RNase-OFF (B); 3: ascorbic acid mixture with 100 mM vitamin C+10 mM $FeCl_3$+0.5% SDS; 4: empty lane; 5: $H_2O$; 6: 10 μg RNase A; 7: empty lane; C: Control of total RNA)

Figure 8:
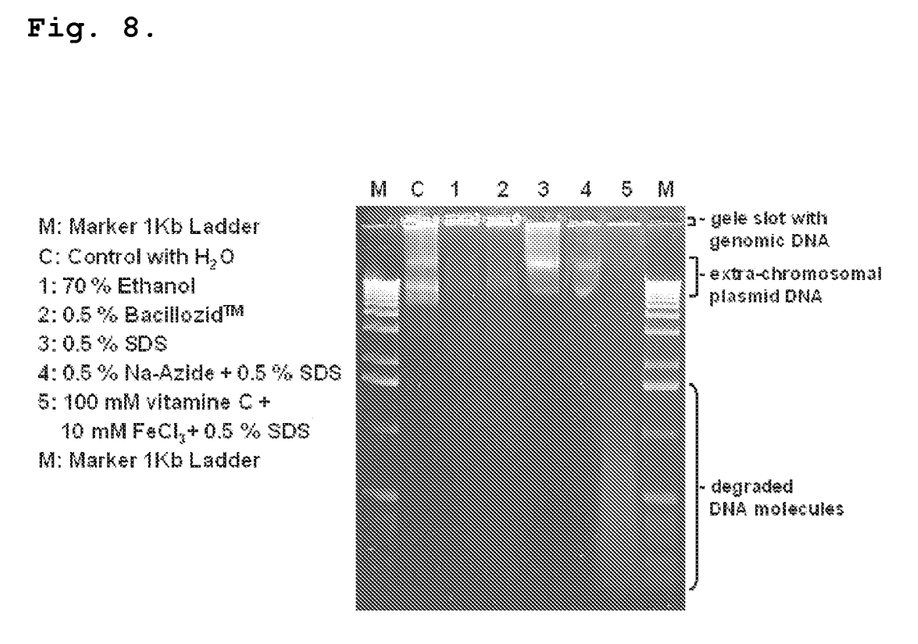
FIG. 8. shows the efficient degradation of genomic DNA and extra chromosomal genetic material inside microorganisms by the new three component system.

FIG. 8 shows the efficient degradation of genomic DNA and extra-chromosomal genetic material inside microorganisms by the new three component system. A recombinant *Escherichia coli* strain with an extra-chromosomal plasmid (YEp351) was grown over night in LB, amp medium. Aliquots of 5 μl from the *E. coli* suspension were treated with 5 μl lysozyme solution (1 mg/ml) for 5 minutes and subsequently incubated with 5 μl of the listed solutions (1-5) for additional 5 minutes. After addition of bromphenol blue the samples were loaded into the gel slots and separated by electrophoresis of the DNA molecules. Only for sample number 5 with the three component system a massive degradation of the DNA molecules is identifiable. For the control with sterile water (C) and for sample 3 and 4 lysis of the cells is observed and therefore the extra-chromosomal plasmid DNA is released and can migrate into the gel. For samples 1 and 2 one observes a precipitation of the lysate and the DNA and therefore consequently all DNA molecules remain at the bottom of the gel slot.

(M: Marker 1 Kb Ladder; C: Control with $H_2O$; 1: 70% Ethanol; 2: 0.5% Bacillozid™; 3: 0.5% SDS; 4: 0.5% Na-Azide+0.5% SDS; 5: 100 mM vitamin C+10 mM $FeCl_3$+ 0.5% SDS; C: Control: 5 μl sterile $H_2O$)

Table 1 shows the test for antimicrobial action of the new three component system.

Freshly grown cultures of the listed microorganisms were adjusted to a cell number of $10^6$ in a 50 μl volume and mixed in a ratio of 1:1 with 50 μl of water, 70% ethanol or the three component system (100 mM ascorbic acid, 10 mM $FeCl_3$ and 0.5% SDS). After an incubation time of 2 minutes the 100 μl samples containing the microorganisms were plated onto the respective growth media. After an incubation period of 1-3 days at 28° C. (*Saccharomyces cerevisiae* and *Candida parapsilosis*) or 37° C. (*Escherichia coli* and *Bacillus subtilis*) the number of grown colonies was determined. In test samples with sterile water all microorganisms survived. Test samples with 70% ethanol or the three component system did not show any living cell colony, indicating that under these conditions all microorganisms were killed.

Table 2 summarizes the preferred composition of the solution with the three component system comprising surface-active substances, vitamins and metal ions for removal of DNA molecules from surfaces and equipments.

List with Explanation of the Abbreviations in the Figures amp: ampicillin
Bacillozid™: commercial anti-bacterial solution
DNase-OFF™: commercial solution for inactivation of DNA
EtBr: ethidium bromide
FAD: Flavine adenine dinucleotide
C: Control
M: Molecular weight marker
PCR: Polymerase Chain Reaction
RNase-OFF™: commercial solution for inactivation of RNases
RNaseA: Ribonuclease A (from bovine pancreas)
RT: Room Temperature
sc: *Saccharomyces cerevisiae*
scIMP2: *Saccharomyces cerevisiae* gene for Inner Membrane Protease 2
scPCP1: *Saccharomyces cerevisiae* gene for Processing of Cytochrome c Peroxidase
SDS: Sodiumdodecylsulfate
TX: TritonX-100 (non-ionic detergent)
YEp351: Yeast Episomal plasmid

TABLE 1

Test for the anti-microbial action of the new three component system.

| microorganisms | $H_2O$ | 70% ethanol | three component system |
|---|---|---|---|
| *Escherichia coli* | $10^6$ | 0 | 0 |
| *Bacillus subtilis* | $10^6$ | 0 | 0 |
| *Saccharomyces cerevisiae* | $10^6$ | 0 | 0 |
| *Candida parapsilosis* | $10^6$ | | 0 |

TABLE 2

Preferred composition of solutions containing the three component system comprising surface-active substances, vitamins and metal ions for the removal of DNA molecules from surfaces and equipment.
composition of the solutions pH range: 2.0 to 8.5
vitamins: 1 mM to 100 mM
metal ions: 1 mM to 50 mM
detergents: 0.1% to 5%

The invention claimed is:
1. A method comprising:
providing a decontamination solution comprising:
at least a synergistic mixture of
a) at least one water-soluble vitamin in concentration from 10 mM to 100 mM,
b) at least one metal ion in concentration from 1 mM to 100 mM, and
c) at least on surface-active substance in concentration from 0.1% to

10% (weight) in relation to the total solution, wherein the synergistic mixture of the decontamination solution is configured to degrade DNA (deoxyribonucleic acid), protein and RNA (ribonucleic acid) on a surface of equipment, and treating the surface of the equipment that is contaminated by proteins, nucleic acid molecules and/or microorganisms comprising proteins and nucleic acid molecules with said decontamination solution resulting in a treated surface, wherein the decontamination solution degrades protein and any DNA and any RNA on the treated surface, and wherein the microorganisms are killed by degrading the proteins and any DNA and any RNA of the microorganisms on the treated surface.

2. The method according to claim 1, wherein the solution is adjusted via a buffer system to a pH value ranging between 2 to 8.5.

3. The method of claim 1, wherein the DNA and the RNA is completely degraded after a residence time of the decontamination solution on the treated surface of 0.5 to 2 minutes at room temperature.

4. A decontamination solution comprising a synergistic mixture, wherein said mixture comprises:
   100 mM vitamin C, 10 mM $FeCl_3$, 0.2% octoxynol 9, and 0.2% polysorbate 20;
   100 mM vitamin C, 10 mM $FeCl_3$, and 0.2% octoxynol 9;
   50 mM vitamin C, 5 mM $FeCl_3$, 0.2% octoxynol 9, and 0.2% polysorbate 20;
   10 mM vitamin C, 10 mM $FeCl_3$, 0.2% octoxynol 9, and 0.2% polysorbate 20;
   100 mM vitamin C, 5 mM $FeCl_3$, 0.2% octoxynol 9, and 0.2% polysorbate 20;
   100 mM Na-ascorbate, 5 or 10 mM $FeCl_3$, 0.2% octoxynol 9, and 0.2% polysorbate 20;
   100 mM thiamin, 5 mM $FeCl_3$, 0.2% octoxynol 9, and 0.2% polysorbate 20;
   100 mM Na-ascorbate, 10 mM $ZnCl_2$, 0.2% octoxynol 9;
   100 mM Na-ascorbate, 10 mM $FeCl_3$, 0.2% octoxynol 9;
   100 mM vitamin C, 10 mM $ZnCl_2$, and 0.2% octoxynol 9; or
   100 mM vitamin C, 10 mM $ZnCl_2$, 0.2% octoxynol 9, and 0.2% polysorbate 20.

5. The decontamination solution of claim 4, wherein said mixture comprises 100 mM vitamin C, 10 mM $FeCl_3$, 0.2% octoxynol 9, and 0.2% polysorbate 20.

6. The decontamination solution of claim 4, wherein said mixture comprises 100 mM vitamin C, 10 mM $FeCl_3$, and 0.2% octoxynol 9.

7. The decontamination solution of claim 4, wherein said mixture comprises 50 mM vitamin C, 5 mM $FeCl_3$, 0.2% octoxynol 9, and 0.2% polysorbate 20.

8. The decontamination solution of claim 4, wherein said mixture comprises 10 mM vitamin C, 10 mM $FeCl_3$, 0.2% octoxynol 9, and 0.2% polysorbate 20.

9. The decontamination solution of claim 4, wherein said mixture comprises 100 mM vitamin C, 5 mM $FeCl_3$, 0.2% octoxynol 9, and 0.2% polysorbate 20.

10. The decontamination solution of claim 4, wherein said mixture comprises 100 mM Na-ascorbate, 5 or 10 mM $FeCl_3$, 0.2% octoxynol 9, and 0.2% polysorbate 20.

11. The decontamination solution of claim 4, wherein said mixture comprises 100 mM thiamin, 5 mM $FeCl_3$, 0.2% octoxynol 9, and 0.2% polysorbate 20.

12. The decontamination solution of claim 4, wherein said mixture comprises 100 mM Na-ascorbate, 10 mM $ZnCl_2$, 0.2% octoxynol 9.

13. The decontamination solution of claim 4, wherein said mixture comprises 100 mM Na-ascorbate, 10 mM $FeCl_3$, 0.2% octoxynol 9.

14. The decontamination solution of claim 4, wherein said mixture comprises 100 mM vitamin C, 10 mM $ZnCl_2$, and 0.2% octoxynol 9.

15. A method comprising:
providing a decontamination solution comprising a synergistic mixture, wherein said mixture comprises:
   100 mM vitamin C, 10 mM $FeCl_3$, 0.2% octoxynol 9, and 0.2% polysorbate 20;
   100 mM vitamin C, 10 mM $FeCl_3$, and 0.2% octoxynol 9;
   50 mM vitamin C, 5 mM $FeCl_3$, 0.2% octoxynol 9, and 0.2% polysorbate 20;
   10 mM vitamin C, 10 mM $FeCl_3$, 0.2% octoxynol 9, and 0.2% polysorbate 20;
   100 mM vitamin C, 5 mM $FeCl_3$, 0.2% octoxynol 9, and 0.2% polysorbate 20;
   100 mM Na-ascorbate, 5 or 10 mM $FeCl_3$, 0.2% octoxynol 9, and 0.2% polysorbate 20;
   100 mM thiamin, 5 mM $FeCl_3$, 0.2% octoxynol 9, and 0.2% polysorbate 20;
   100 mM Na-ascorbate, 10 mM $ZnCl_2$, 0.2% octoxynol 9;
   100 mM Na-ascorbate, 10 mM $FeCl_3$, 0.2% octoxynol 9;
   100 mM vitamin C, 10 mM $ZnCl_2$, and 0.2% octoxynol 9; or
   100 mM vitamin C, 10 mM $ZnCl_2$, 0.2% octoxynol 9, and 0.2% polysorbate 20.

16. The method of claim 15, wherein said mixture comprises 100 mM vitamin C, 10 mM $FeCl_3$, 0.2% octoxynol 9, and 0.2% polysorbate 20.

17. The method of claim 15, wherein said mixture comprises 100 mM vitamin C, 10 mM $FeCl_3$, and 0.2% octoxynol 9.

18. The method of claim 15, wherein said mixture comprises 50 mM vitamin C, 5 mM $FeCl_3$, 0.2% octoxynol 9, and 0.2% polysorbate 20.

19. The method of claim 15, wherein said mixture comprises 10 mM vitamin C, 10 mM $FeCl_3$, 0.2% octoxynol 9, and 0.2% polysorbate 20.

20. The method of claim 15, wherein said mixture comprises 100 mM vitamin C, 5 mM $FeCl_3$, 0.2% octoxynol 9, and 0.2% polysorbate 20.

21. The method of claim 15, wherein said mixture comprises 100 mM Na-ascorbate, 5 or 10 mM $FeCl_3$, 0.2% octoxynol 9, and 0.2% polysorbate 20.

22. The method of claim 15, wherein said mixture comprises 100 mM thiamin, 5 mM $FeCl_3$, 0.2% octoxynol 9, and 0.2% polysorbate 20.

23. The method of claim 15, wherein said mixture comprises 100 mM Na-ascorbate, 10 mM $ZnCl_2$, 0.2% octoxynol 9.

24. The method of claim 15, wherein said mixture comprises 100 mM Na-ascorbate, 10 mM $FeCl_3$, 0.2% octoxynol 9.

25. The method of claim 15, wherein said mixture comprises 100 mM vitamin C, 10 mM $ZnCl_2$, and 0.2% octoxynol 9.

26. The method of claim 15, wherein said mixture comprises 100 mM vitamin C, 10 mM $ZnCl_2$, 0.2% octoxynol 9, and 0.2% polysorbate 20.

* * * * *